United States Patent [19]

Le Tourneau et al.

[11] Patent Number: 4,734,430

[45] Date of Patent: Mar. 29, 1988

[54] DIPYRAZOLES AND THEIR USE AS BRONCHODILATORS

[75] Inventors: Michael E. Le Tourneau; Norton P. Peet, both of Indianapolis, Ind.

[73] Assignee: Merrell Dow Pharmaceuticals Inc., Cincinnati, Ohio

[21] Appl. No.: 7,305

[22] Filed: Jan. 27, 1987

[51] Int. Cl.$^4$ .................. A61K 31/415; C07D 231/54; C07D 231/56

[52] U.S. Cl. .................................. 514/406; 548/369; 548/371

[58] Field of Search .................. 548/371, 369; 514/406

[56] References Cited

U.S. PATENT DOCUMENTS 3,404,157 10/1968 McEvoy et al. .................... 548/371
4,515,948 5/1985 Kompis et al. ..................... 544/325

OTHER PUBLICATIONS

G. Spiteller, G. Schmidt, H. Budzikiewicz, F. Wessely, CA54:17377i (1960).

F. Wessely, H. Budzikiewicz, H. Janda, CA55:25922b (1961).

I. A. Strakova, A. Ya Strakov, E. Gudriniece, Latv. PSR, *Zinat Akad Vestis, Kim Ser*, 5:610–14 (1974); (CA82:43247w) (1975).

E. Gudriniece, I. A. Strakova, A. Ya Strakov, CA82:4172y (1975).

*Primary Examiner*—Henry R. Jiles
*Assistant Examiner*—Kurt G. Briscoe
*Attorney, Agent, or Firm*—John J. Kolano

[57] ABSTRACT

A group of variously methyl-substituted[1,2-c:3,4-c']dipyrazoles, cyclohepta[1,2-c:3,4-c']dipyrazoles, and cyclopenta[1,2-c:3,4-c']dipyrazoles useful as bronchodilators are described herein. The compounds are prepared by reacting a 1,3-diketone with hydrazine or methylhydrazine to give tricyclic products optionally followed by catalytic dehydrogenation and/or alkylation with a strong base and methyl iodide to give various other compounds within the scope of the invention.

17 Claims, No Drawings

DIPYRAZOLES AND THEIR USE AS BRONCHODILATORS

The present invention is directed to a group of compounds which are variously methylated and variously hydrogenated benzodipyrazoles, cycloheptadipyrazoles, and cyclopentadipyrazoles. More particularly, the present invention is directed to a group of compounds having the following general formula:

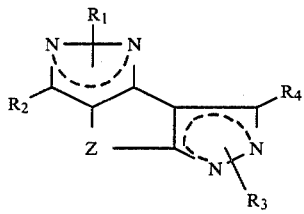

wherein $R_1$, $R_2$, $R_3$ and $R_4$ are each independently hydrogen or methyl with $R_1$ and $R_3$ being positioned on one of the nitrogens in their respective rings with the other nitrogen then being doubly bonded to the adjacent carbon; the dotted lines indicate the presence of two conjugated double bonds with the specific position of the double bonds being determined by the position of the $R_1$ or $R_3$ substituents; Z is —CH=CH— or —[$C_nH_{(2n-q)}(CH_3)_q$]—, wherein n is 1, 2 or 3; q is 0, 1 or 2; and $C_nH_{(2n-q)}$ is a straight-chain alkylene. By straight-chain alkylene is meant an alkylene containing no side chains between the free valences. Such alkylenes are specifically exemplified by methylene, ethylene and trimethylene. These alkylenes can be substituted by the group $(CH_3)_q$ referred to earlier. The present invention further encompasses the pharmaceutically acceptable acid addition salts of the aforesaid compounds.

Acid addition salts of the aforesaid compounds with pharmaceutically acceptable acids are equivalent to the amines for the purposes of this invention. Illustrative of such salts are the salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicyclic, 4-aminosalicyclic, 2-phenoxybenzoic, 2-acetoxybenzoic, mandelic and like acids; and with organic sulfonic acids such as methanesulfonic acid and p-toluenesulfonic acid.

Preferred embodiments of the present invention are those compounds wherein Z is —$(CH_2)_n$— wherein n is 1, 2 or 3. Within this group, still further preferred embodiments are those compounds in which Z is —$CH_2$—$CH_2$—. Still further preferred within this group are compounds having the following general formula:

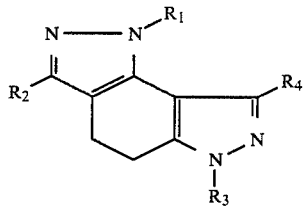

wherein the various R-groups are defined as above. Yet other preferred embodiments of the present invention are those compounds wherein Z is —CH=CH—.

The compounds of the present invention are prepared by the reaction of a hydrazine of the formula

$R_1$—NHNH$_2$ wherein $R_1$ is hydrogen or methyl, with a 1,3-diketone of the formula:

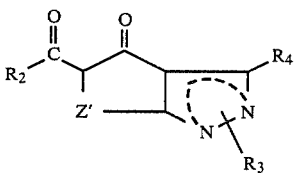

wherein $R_2$ and $R_4$ are each independently hydrogen or methyl and $R_3$ is hydrogen, methyl or benzyl, with $R_3$ being positioned on one of the nitrogens in the pyrazole ring with the other nitrogen being doubly bonded to the adjacent carbon; the dotted line indicates the presence of two conugated double bonds with the specific position of the double bonds being determined by the position of the $R_3$ substituent; and Z' is —[$C_nH_{(2n-q)}(CH_3)_q$]— wherein n is 1, 2 or 3 and q is 0, 1 or 2. The reaction is carried out with heating in an inert solvent such as an alcohol, with methanol being preferred. When $R_3$ is benzyl, the product is treated with sodium in liquid ammonia to give the corresponding product in which $R_3$ is hydrogen. When $R_1$ or $R_3$ is hydrogen, the product is further optionally treated with sodium hydride and methyl iodide in an inert solvent such as dimethylformamide to give the corresponding compounds wherein $R_1$ or $R_3$ is methyl. When the process gives a mixture of products with substitution on either nitrogen in the rings in question, the resultant mixture is separated by crystallization or chromatography. When Z' is —$CH_2CH_2$—, the product can be further optionally dehydrogenated using palladium on charcoal catalyst to give the product in which Z is —CH=CH—.

When $R_1$ in the starting hydrazine is methyl, the reaction may give a single product or it may give a mixture of two products with the methyl substituent on either of the two nitrogens in the newly formed (pyrazole) ring. When such a mixture of products is obtained, the individual pure compounds can be obtained by standard procedures such as crystallization or chromatography.

The diketone starting material shown above enolizes readily so that, for example, when $R_2$ is hydrogen, the

group can exist in the alternative hydroxymethylene form (HOCH=) and such a hydroxymethylene form may be preferred.

The preparation of the pyrazolo 1,3-diketones used as the starting material above can be summarized by the following reaction scheme:

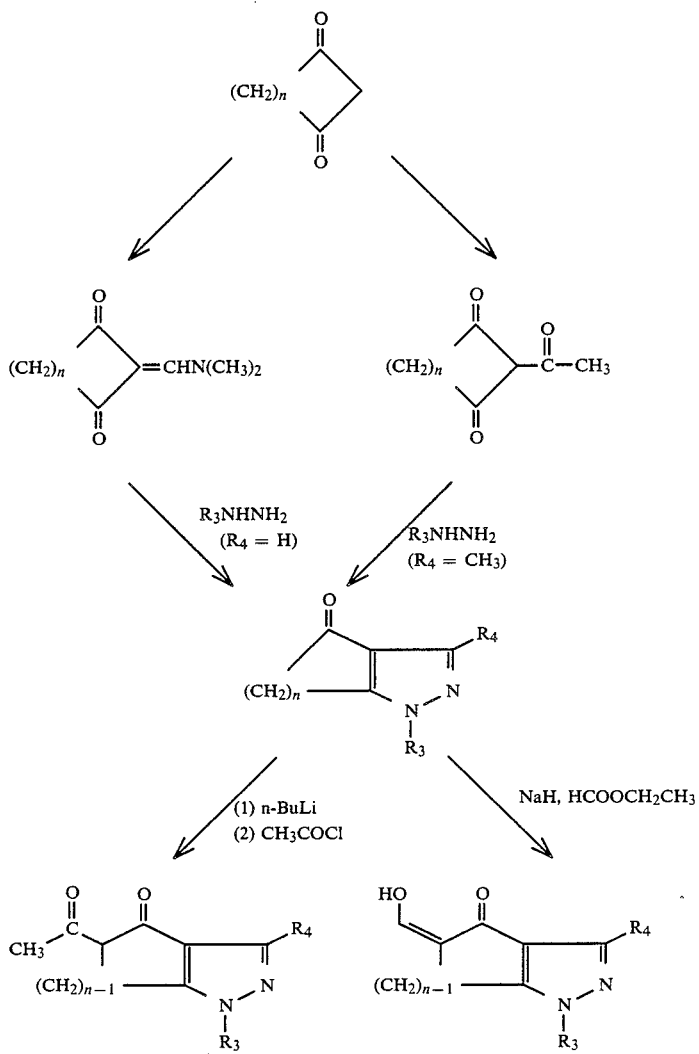

An appropriate cyclic 1,3-diketone serves as the common starting material for all of the preparations. This ketone can be converted to the corresponding 2-dimethylaminomethylene or 2-acetyl compound by standard procedures. Reaction of either of these materials with an appropriate hydrazine (i.e., hydrazine, methylhydrazine or benzylhydrazine) brings about cyclization and formation of a pyrazole ring which may be substituted on one of the nitrogens depending on the hydrazine starting material used. In the case of the 2-acetylcycloalkanedione starting material, the product has a methyl substituent at the 3-position of the pyrazole ring, while use of the dimethylaminomethylene starting material gives the product without such substitution. An acetyl or formyl group can then be introduced alpha to the carbonyl group in the carbocyclic ring by standard procedures to give the desired pyrazole diketone. More particularly, in the case of the acetyl group, acetyl chloride and a strong base such as lithium diisopropylamine or lithium bis(trimethylsilyl)amide are used. In the case of the introduction of the formyl group, ethyl formate and a strong base such as sodium hydride are used. Although the group introduced here has been referred to as formyl, the fact of the matter is that, as indicated earlier, such a group enolizes readily in the structure in question so that the compounds could also be described as having a hydroxymethylene group alpha to the cyclic ketone.

The substituted dipyrazole compounds as described herein are bronchodilators and are thus useful in the treatment of bronchial disorders such as bronchial asthma. The present invention is further directed to a method of effecting bronchodilation.

In practicing the method of this invention, an effective bronchodilating amount of 1 or more substituted dipyrazoles of this invention is administered internally to a mammal in need thereof by a route effective to bring the compound into contact with the bronchial and tracheal tissues of the mammal. Administration can be carried out either by a parenteral route, such as by intravenous, intraperitoneal or intramuscular injection, or by introduction into the gastrointestinal tract via oral or rectal administration, for example, in order to bring about such contact via the blood stream, or by intratracheal administration, by inhalation of a solution in the form of a spray, for example.

The effective bronchodilating amount of the compound, that is, the amount sufficient to inhibit or alleviate bronchial spasm, depends on various factors such as the size, type and age of the animal to be treated, the particular compound or pharmacologically-acceptable salt employed, the route and frequency of administration, the severity of any spasm and the causative agent involved, and the time of administration. In particular cases, the dosage to be administered can be ascertained by conventional range finding techniques, for example, by observing the bronchodilator activity produced at different dosage rates. More specifically, the compounds can be administered at dosage rates ranging from about 0.2 to about 100 milligrams of substituted dipyrazole compound per kilogram of animal body weight with other ranges being from about 0.5 to about 20 or from 1 to about 5 milligrams per kilogram. It is generally desirable to administer individual dosages at the lowest amount which provides the desired protection from bronchial spasm consonant with a convenient dosing schedule. Dosage units adaptable to oral administration such as tablets, capsules, lozenges, elixirs, syrups and the like are generally preferred and the active compound can be formulated in conventional time release capsule or tablet formulations although injectable compositions or sprays and aerosols for inhalation are preferred when rapid action is desired. In an example of an individual dosage unit, a tablet would contain 200 mg of active ingredient and would be administered 1 to 6 times daily or, preferably, 2 to 4 times daily.

In practicing the method of the invention, the active ingredient is preferably incorporated in a composition comprising a pharmaceutical carrier and from about 5 to about 90 percent by weight of the substituted dipyrazole compound or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, lozenges, troches, suppositories, elixirs, syrups, emulsions, dispersions, wettable and effervescent powders, sterile injectable compositions and solutions for sprays, and can contain suitable excipients known to be useful in the preparation of the particular type of compositions desired. Suitable pharmaceutical carriers and formulation techniques are found in standard texts, such as *Remington's Pharmaceutical Sciences*, Mack Publishing Company, Easton, Pa.

In evaluating bronchodilator activity, test compounds were administered to guinea pigs by intraperitoneal injection or orally and the guinea pigs were challenged by exposure to a histamine aerosol at periods ranging from 15 minutes to 4 hours later. Untreated animals collapsed when exposed to the histamine aerosol. In the test procedure, the animals were observed and times to collapse were recorded. The collapse times observed were then compared statistically with control animals treated with water alone, with the control group usually being a long-term cumulative control. The actual dose of test compound administered was generally 30% of the $LD_{50}$ administered intraperitoneally Some specific doses of compounds used in the testing (i.p. administration) are as follows:

1,4,5,6-Tetrahydro-1,6-dimethylbenzo[1,2-c:3,4-c']dipyrazole monohydrochloride; 82 mg/kg.
1,4,5,6-Tetrahydro-3,6-dimethylbenzo[1,2-c:3,4-c')dipyrazole; 163 mg/kg.
2,4,5,6-Tetrahydro-2,3,6-trimethylbenzo[1,2-c:3,4-c']1dipyrazole; 113 mg/kg.
1,4,5,6-Tetrahydro-1,8-dimethylbenzo[1,2-c:3,4-c']1dipyrazole; 41 mg/kg.
1,6-Dihydro-3,6-dimethylbenzo[1,2-c:3,4-c']dipyrazole; 82 mg/kg.
1,6-Dihydro-3,8-dimethylbenzo[1,2-c:3,4-c']dipyrazole; 32 mg/kg.
4,5,6,7-Tetrahydro-7-methyl-1H-cyclohepta[1,2-c:3,4c']dipyrazole; 82 mg/kg.
4,5,6,7-Tetrahydro-3,7-dimethyl-1H-cyclohepta[1,2c:3,4-c']dipyrazole monohydrochloride; 110 mg/kg.

When tested by the procedure described above, the compounds of the present invention were found to produce a bronchodilating effect.

The following examples are presented to illustrate the present invention but they should not be construed as limiting it in any way.

EXAMPLE 1

A mixture was prepared from 90 grams of 1,3-cyclohexanedione and 225 ml of N,N-dimethylformamide dimethyl acetal and heated at reflux for 90 minutes. Excess solvent was removed under reduced pressure and the residue was triturated in hot ethyl acetate to give 2-dimethylaminomethylene-1,3-cyclohexanedione as rust colored crystals melting at about 114.5°–116° C.

EXAMPLE 2

To an ice-cold solution of 67 grams of 2-dimethylaminomethylene-1,3-cyclohexanedione in 600 ml of methanol was added slowly a solution of 21.3 ml of methylhydrazine in 200 ml of methanol and the resulting solution was heated at reflux for 2 hours. The solvent was removed under reduced pressure and the residue was triturated with ethyl ether to give 1,5,6,7-tetrahydro-1-methyl-4H-indazol-4-one as a tan crystalline solid melting at about 88°–91° C.

A mixture of 7.8 grams of benzylhydrazine dihydrochloride, 100 ml of methanol and 16 ml of 5 N sodium hydroxide was added slowly to an ice-cold solution of 6.7 grams of 2-dimethylaminomethylene-1,3-cyclohexanedione in 100 ml of methanol. The reaction mixture was heated at reflux for 90 minutes, the solvent was removed under reduced pressure, and the residue was diluted with water. The resultant slurry was extracted several times with dichloromethane and the combined dichloromethane extracts were dried over magnesium sulfate and concentrated under reduced pressure to leave an amber oil which crystallized on standing. The product obtained in this way was 1,5,6,7-tetrahydro-1-benzyl-4H-indazol-4-one melting at about 55°–59° C.

To an ice-cold solution of 33.3 grams of 2-acetyl-1,3-cyclohexanedione in 400 ml of methanol was added dropwise a solution of 7.2 ml of hydrazine in 50 ml of methanol and the resulting reaction mixture was heated at reflux for 20 hours. The solvent was then removed under reduced pressure and the residue was triturated in ethyl ether to give 1,5,6,7-tetrahydro-3-methyl-4H-indazol-4-one as a yellow crystalline solid melting at about 154°–157° C.

A solution of 11 ml of methylhydrazine in 50 ml of methanol was added dropwise to an ice-cold solution of 30 grams of 2-acetyl-1,3-cyclohexanedione in 200 ml of methanol and the reaction mixture was heated at reflux for 90 minutes. The solvent was removed under reduced pressure and the residue was triturated in hexane and cooled to give a clammy tan solid. This crude product was recrystallized from a mixture of toluene and hexane to give 1,5,6,7-tetrahydro-1,3-dimethyl-4H-indazol-4-one as a yellow crystalline solid melting at about 82.5°–84° C.

EXAMPLE 3

To an ice-cold solution of 21 grams of 2-acetyl-1,3-cycloheptanedione in 180 ml of methanol was added, dropwise, a solution of 6.2 ml of methylhydrazine in 30 ml of methanol. The resulting reaction mixture was heated at reflux for 1 hour and the solvent was then removed under reduced pressure. The residual material was partitioned between dichloromethane and brine, the aqueous layer was extracted twice with dichloromethane, and the combined organic layers were dried over magnesium sulfate. The solvent was removed under reduced pressure to leave a dark oil which crystallized on standing. The solid was recrystallized from a mixture of ether and hexane to give 5,6,7,8-tetrahydro-1-methyl-4(1H)-cycloheptapyrazolone as a yellow crystalline solid melting at about 95°–97° C.

The mother liquor from the above purification was concentrated under reduced pressure to give a dark oil which was a 60:40 mixture of 5,6,7,8-tetrahydro-2-methyl-4(2H)cycloheptapyrazolone and the 1-methyl compound described earlier. A solution of this oil (10.4 g) in 200 ml of tetrahydrofuran was mixed with 3.0 g of sodium hydride, 15 ml of ethyl formate and 2 drops of ethanol and heated at reflux for 2 hours and then partitioned between ether and water. The aqueous layer was washed three times with dichloromethane and once with ether, and then acidified to a pH of 5 with dilute hydrochloric acid. The mixture was extracted exhaustively with dichloromethane and the combined organic extracts were dried over magnesium sulfate and concentrated in vacuo to provide a dark oil. The oil was diluted with 300 ml of methanol and treated dropwise with 1.9 ml of hydrazine. The solution was heated on a steam bath for 45 minutes and the solvent was removed in vacuo to provide a thick, dark oil. This oil was dissolved in 200 ml of 2-propanol and the mixture was acidified with ethanolic hydrogen chloride to provide a brown solid. This solid was recrystallized from isopropanol-ethanol to afford 4,5,6,8-tetrahydro-8-methyl-1H-cyclohepta[1,2-c:3,4c']dipyrazole monohydrochloride as a brown powder melting at about 234°–239° C. with decomposition.

EXAMPLE 4

A mixture of 1.3 grams of benzylhydrazine dihydrochloride and 2.8 ml of 5 N sodium hydroxide in 10 ml of methanol was added to an ice-cold solution of 2-dimethylaminomethylene-1,3-cyclopentanedione in 20 ml of methanol. The mixture was heated at reflux for 2 hours and concentrated under reduced pressure. The residue was extracted several times with dichloromethane and the combined dichloromethane extracts were dried over magnesium sulfate and concentrated under reduced pressure to give a fluffy yellow solid. This was recrystallized from a mixture of toluene and hexane to give 2-[(2-benzylhydrazino)methylene]-1,3-cyclopentanedione melting about 164° C. with decomposition.

A mixture of 1 gram of the product obtained in the preceding paragraph, 50 mg of 4-toluenesulfonic acid monohydrate, and 200 ml of toluene was heated at reflux for 16 hours. A Dean-Stark trap was used for the first few hours to collect water that formed. At the end of the reflux period, the solvent was removed under reduced pressure and the residue was flash-chromatographed (10% methanol in dichloromethane) on silica gel to give a light brown solid. This was further purified by a second flash-chromatography (5% methanol in dichloromethane) on silica gel to give 1-benzyl-5,6-dihydro-4(1H)-cyclopentapyrazolone melting at about 92°–93° C.

EXAMPLE 5

A stirred mixture 16.8 grams of 1,5,6,7-tetrahydro-1-methyl-4H-indazol-4-one, 6 grams of 97% sodium hydride, 15 ml of ethyl formate, 3 drops of ethanol and 200 ml of toluene was heated at reflux for 16 hours. The mixture was then cooled and extracted twice with water and the aqueous extracts were combined and washed with ethyl ether. The aqueous solution was acidified with 5 N hydrochloric acid to a pH of approximately 4 and the resultant slurry was extracted several times with dichloromethane. The combined dichloromethane extracts were dried over magnesium sulfate and concentrated under reduced pressure to leave a residual dark oil. The oil was triturated with a 50:50 mixture of hexane and ethyl ether to give 1,5,6,7-tetrahydro-5-hydroxymethylene-1-methyl-4H-indazol-4-one melting at about 93°–95° C.

A mixture of 7.8 grams of 1-benzyl-1,5,6,7-tetrahydro-4H-indazol-4-one, 2.8 grams of sodium hydride (60% suspension in mineral oil), 10 ml of ethyl formate, 2 drops of ethanol and 100 ml of tetrahydrofuran was stirred at reflux for 1 hour and then cooled. Water (300 ml) and 100 ml of ethyl ether were added and the mixture was stirred briefly. The layers were separated and the aqueous layer was washed with ethyl ether and acidified with concentrated hydrochloric acid to a pH of about 4. The resulting slurry was extracted several times with dichloromethane and the combined organic extracts were dried over magnesium sulfate and concentrated under reduced pressure to give 1-benzyl1,5,6,7-tetrahydro-5-hydroxymethylene 4H-indazol-4-one as an amber oil.

The procedure of the preceding paragraph was repeated using 15.2 grams of 1,5,6,7-tetrahydro-1,3-dimethyl-4H-indazol-4-one as the indazolone and a reflux time of 3 hours. The product thus obtained was 1,5,6,7-tetrahydro-5-hydroxymethylene-1,3-dimethyl-4H-indazol-4-one as a brown solid melting at about 108°–111.5° C.

To an ice-cold solution of 13.9 ml of diisopropylamine in 50 ml of anhydrous tetrahydrofuran there was added, by syringe, 38 ml of 2.6 N butyllithium in hexane. The mixture was cooled to −78° C. and a solution of 4.5 grams of 1,5,6,7-tetrahydro-3-methyl-4H-indazol-4-one was added dropwise. The mixture was stirred at −78° C. for 30 minutes and a solution of 10 ml of ethyl formate in 30 ml of anhydrous tetrahydrofuran was added dropwise. When the addition was complete, the reaction was allowed to warm to 0° C. and it was quenched by the dropwise addition of water (200 ml). After the mixture was stirred vigorously for a few minutes, the two layers which formed were separated. The aqueous layer was washed with ethyl ether and then acidified to a pH of about 4 with 5 N hydrochloric acid. The slurry which formed was extracted several times with dichloromethane and the combined extracts were dried and concentrated under reduced pressure to give 1,5,6,7-tetrahydro-5-hydroxymethylene-3-methyl-4H-indazol-4-one as a clammy yellow semi-solid.

n-Butyllithium (23.8 ml of a 2.60 M solution in hexane) was added slowly to an ice-cold solution of 8.7 ml of N,N-diisopropylamine in 30 ml of anhydrous tetrahydrofuran. The solution was stirred at 0° C. for 15 minutes and treated with 10.8 ml of hexamethylphosphoramide; it was then stirred at 0° C. for 15 minutes and cooled to −78° C. A solution of 5 g of 1,5,6,7-tetrahydro-1,6,6-trimethyl-4H-indazol-4-one in 150 ml of anhydrous tetrahydrofuran was added dropwise, followed by the dropwise addition of 8.9 ml of ethyl formate. The reaction was allowed to warm to room temperature and was stirred for 20 hours and 150 ml of water was added and the mixture was extracted with dichloromethane. The aqueous layer was acidified with aqueous hydrochloric acid and extracted exhaustively with dichloromethane. The combined extracts were dried over magnesium sulfate and concentrated in vacuo to provide a dark oil which crystallized upon standing. Flash chromatography of this material (10% acetone in dichloromethane) on silica gel provided product as light yellow crystals. Recrystallization from hexane/toluene gave 4,5,6,7-tetrahydro-1,6,6-trimethyl-4-oxo-1H-indazole-5-carboxaldehyde melting at about 131°–132° C.

EXAMPLE 6

A mixture of 7 grams of 5,6,7,8-tetrahydro-1-methyl4(1H)-cycloheptapyrazolone, 2.3 grams of sodium hydride (97%), 12 ml of ethyl formate, 2 drops of ethanol and 100 ml of tetrahydrofuran was heated at reflux for 3 hours. The mixture was then cooled and partitioned between water and ether. The aqueous layer was washed once with ether and acidified to a pH of 5 with 1 N hydrochloric acid. The white precipitate which formed was separated by filtration and dried to give 5,6,7,8-tetrahydro-5-hydroxymethylene-1-methyl-4(1H)-cycloheptapyrazolone as a cream colored powder melting at about 133°–135° C.

EXAMPLE 7

Sodium hydride (1.44 grams of a 60% suspension in mineral oil), 1.46 ml of ethyl formate and 3 drops of ethanol were combined in 150 ml of anhydrous tetrahydrofuran and stirred at room temperature for 30 minutes. A solution of 4 grams of 1-benzyl-5,6-dihydro-4(1H)-cyclopentapyrazolone in 50 ml of anhydrous tetrahydrofuran was added dropwise and the reaction mixture was heated at reflux for 16 hours. An additional 1.44 grams of sodium hydride suspension and 1.46 ml of ethyl formate were then added and the reaction mixture was heated at reflux for 2 hours. The mixture was cooled, diluted with 150 ml of water, and washed with ethyl ether. The aqueous layer was acidified with aqueous hydrochloric acid and the solid which formed was collected by filtration to give 1-benzyl-5,6-dihydro-5-hydroxymethylene-4(1H)-cyclopentapyrazolone as a tan solid melting at about 171°–172° C.

EXAMPLE 8

To an ice-cold solution of 97 ml of diisopropylamine in 300 ml of anhydrous tetrahydrofuran was added, via syringe, 280 ml of 2.5 M n-butyllithium in hexane The mixture was cooled to −78° C. and to it was added a solution of 47.2 grams of 1,5,6,7-tetrahydro-1-methyl-4H-indazol-4one in 180 ml of anhydrous tetrahydrofuran. The reaction was stirred for 20 minutes at −78° C. and then a solution of 29 ml of acetyl chloride in 30 ml of anhydrous tetrahydrofuran was added. The mixture was allowed to warm to −15° C. and it was quenched by the dropwise addition of water (120 ml). The resulting mixture was stirred vigorously for several minutes and diluted with an additional 800 ml of water. The layers were separated and the aqueous portion was washed several times with dichloromethane. The aqueous solution was then acidified to a pH of about 4 with concentrated hydrochloric acid and the slurry which formed was extracted several times with dichloromethane. The combined dichloromethane extracts were dried over magnesium sulfate and concentrated under reduced pressure to give a residual dark oil. This oil was flash chromatographed (10% acetone in dichloromethane) to give a yelow oil which crystallized on standing. The product obtained in this way was 5-acetyl-1,5,6,7-tetrahydro-1-methyl-4H-indazol-4-one melting at about 66°–72° C.

When the procedure of the preceding paragraph was repeated using 1,5,6,7-tetrahydro-3-methyl-4H-indazol-4-one as the starting material instead of the 1-methyl compound, the crude product obtained was an amber oil. This oil was flash chromatographed (9% 2-propanol in dichloromethane) to give 5-acetyl-1,5,6,7-tetrahydro-3-methyl-4H-indazol-4-one as an oily solid.

When the procedure in the first paragraph above was repeated using 5,6,7,8-tetrahydro-1-methyl-4(1H)-cycloheptapyrazolone in place of the indazolone, the product obtained was 5-acetyl-5,6,7,8-tetrahydro-1-methyl-4(1H)-cycloheptapyrazolone.

To a solution of 321 ml of 1.0 N lithium bis(trimethylsilyl)amide in 350 ml of anhydrous tetrahydrofuran maintained at −78° C, there was added dropwise a solution of 33 g of 1-benzyl-1,5,6,7-tetrahydro-4H-indazol-4-one in 150 ml of anhydrous tetrahydrofuran. The mixture was stirred at −78° C. for 10 minutes and then a solution of 11.4 g of acetyl chloride in 120 ml of anhydrous tetrahydrofuran was added. The reaction mixture was worked up in the same manner as described in the first paragraph of this example to give 5-acetyl-1-benzyl-1,5,6,7-tetrahydro-4H-indazol-4one as a yellow oil which crystallized on standing.

EXAMPLE 9

To a ice-cold solution of 27.0 ml of 2.6 M n-butyllithium (in hexane) in 200 ml of anhydrous tetrahydrofuran, there was added, slowly, 9.8 ml of diisopropylamine. The mixture was cooled to −78° C. and a solution of 5.5 g of 5,6,7,8-tetrahydro-1-methyl-4(1H)-cycloheptapyrazolone in 50 ml of anhydrous tetrahydrofuran was added dropwise. The reaction was stirred at −78° C. for 20 minutes and then a solution of 3.6 ml of acetyl chloride in 25 ml of anhydrous tetrahydrofuran was added dropwise. The reaction was warmed to −15° C. and quenched by the dropwise addition of 100 ml of water. The resulting mixture was stirred vigorously as an additional 500 ml of water was added. The aqueous layer was then separated from the mixture, washed several times with ether, and acidified to a pH of about 4 with 5 N hydrochloric acid. The slurry which formed was extracted exhaustively with dichloromethane and the combined extracts were dried over magnesium sulfate. Removal of the solvent under reduced pressure left a residue of 5-acetyl-5,6,7,8-tetrahydro-1-methyl-4(1H)-cycloheptapyrazolone as a gummy yellow solid.

EXAMPLE 10

A solution of 3.2 ml of methylhydrazine in 30 ml of methanol was added dropwise to an ice-cold solution of 10.5 g of 1,5,6,7-tetrahydro-5-hydroxymethylene-1-methyl-4H-indazol-4-one in 200 ml of methanol. The reaction was heated at reflux for 3.5 hours and the solvent was then removed under reduced pressure. The residue was triturated with a mixture of ether and ethanol to give a crude tan solid. This solid was dissolved in a mixture of ether and ethanol and acidified with ethereal hydrogen chloride. The yellow precipitate which formed was separated by filtration and recrystallized from a mixture of ethanol and propanol to give 1,4,5,6-tetrahydro-1,6-dimethylbenzo[1,2-c:3,4-c']dipyrazole monohydrochloride as a yellow crystalline solid melting at about 222°-226° C. with decomposition (51% yield). This compound has the following structural formula:

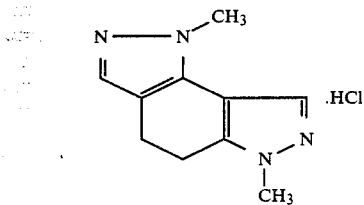

EXAMPLE 11

When the general procedure as described in Example 10 was repeated using the appropriate pyrazole 1,3-diketone and the appropriate hydrazine, the specific compounds listed below were obtained. The listing includes additional special details with regard to the treatment of the crude product obtained from the reaction mixture.

1,4,5,6-Tetrahydro-6-methylbenzo[1,2-c:3,4-c']-dipyrazole as a tan crystalline solid melting at about 242°-245° C. In this case, the crude product was treated with ethyl ether and cooled to give a brown solid (yield, 80%) which was recrystallized from 2-propanol.

1,4,5,6-Tetrahydro-3,6-dimethylbenzo[1,2-c:3,4-c']dipyrazole as light-tan crystals melting at about 184°-186° C. The initial crude product was triturated in ethyl ether and ethanol to give a yellow solid (81% yield) which was recrystallized from toluene.

1,4,5,6-Tetrahydro-8-methylbenzo[1,2-c: 3,4-c']-dipyrazole as a yellow powder melting at about 224°-226.5° C. The initial crude product was flash chromatographed (10% methanol in dichloromethane) to give the product (64% yield).

1,4,5,6-Tetrahydro-6,8-dimethylbenzo[1,2-c:3,4-c')]dipyrazole as a light-tan powder melting at about 212°-213° C. (71% yield). The initial crude product was treated with ethyl ether and cooled to give a tan solid which was recrystallized from a mixture of ethanol and water.

1,4,5,6-Tetrahydro-1,6,8-trimethylbenzo[1,2-c:3,4-c']-dipyrazole as tan crystals melting at about 166°-167.5° C. (53% yield). The initial crude product was triturated in ethyl ether and cooled to give a tan solid which was recrystallized from toluene.

1,4,5,6-Tetrahydro-1,8-dimethylbenzo[1,2-c:3,4-c']dipyrazole as a cream colored powder melting at about 174.5°-177° C. In this case, trituration of the initial crude product in warm ethyl ether followed by cooling gave a tan powder (53% yield) which was recrystallized from toluene.

1,4,5,6-Tetrahydro-3,8-dimethylbenzo[1,2-c:3,4-c']-dipyrazole melting at about 257°-258° C. with decomposition. The initial crude product was triturated with ethyl ether to give a yellow powder (94% yield) which was recrystallized from a mixture of ethanol and water 1,4,5,6-Tetrahydro-4,4,6-trimethylbenzo[1,2-c:3,4c']dipyrazole melting at about 232°-234° C. The initial crude product was triturated with ethyl ether to give tan crystals (75% yield) which were recrystallized from ethyl acetate.

6-Benzyl-1,4,5,6-tetrahydro-1-methylbenzo[1,2-c:3,4c']dipyrazole melting at about 94°-97.5° C. (68% yield). In this case, the initial crude product was flash chromatographed (20% acetone in methylene chloride) to give the indicated product.

6-Benzyl-1,4,5,6-tetrahydrobenzo[1,2-c:3,4-c']dipyrazole as yellow crystals melting at about 217°-219° C. The initial crude product was triturated in ethyl ether to give a yellow powder (84% yield) which was recrystallized from a mixture of ethanol and water.

6-Benzyl-1,4,5,6-tetrahydro-3-methylbenzo[1,2-c:3,4c']dipyrazole as tan crystals melting at about 182°-184° C. Trituration of the initial crude product in ethyl ether gave a tan powder (79% yield) which was recrystallized from toluene.

2,4,5,6-Tetrahydro-2,3,6-trimethylbenzo[1,2-c:3,4c']dipyrazole as yellow crystals (60% yield) melting at about 172°-176° C.

EXAMPLE 12

Hydrazine (0.5 ml) was added slowly to a warm solution of 3 g of 5,6,7,8-tetrahydro-5-hydroxymethylene-1-methyl-4(1H)-cycloheptapyrazolone in 90 ml of methanol. The reaction was heated at reflux for 30 minutes and the solvent was removed under reduced pressure. The residue was triturated in warm ether to give 4,5,6,7-tetrahydro-7-methyl-1H-cyclohepta[1,2-c:3,4 c']dipyrazole as a tan powder (96% yield) melting at about 153°-155° C.

A solution of 4 g of 5-acetyl-5,6,7,8-tetrahydro-1 -methyl-4(1H)-cycloheptapyrazolone and 0.7 ml of hydrazine in 50 ml of methanol was heated at reflux for 30 minutes and the solvent was removed in vacuo. The residue was flash chromatographed (10% methanol in dichloromethane) on silica gel to provide crude product as a gummy, yellow solid. This solid was dissolved in 2-propanol and the mixture was acidified with ethereal hydrogen chloride 4,5,6,7-Tetrahydro-3,7-dimethyl-1H-cyclohepta[1,2-c: 3,4c']dipyrazole monohydrochloride (62% yield) was collected by filtration as a yellow powder melting at about 277°-280° C. with decomposition.

To an ice-cold solution of 4 g of 5,6,7,8-tetrahydro-5-hydroxymethylene-1-methyl-4(1H) cycloheptapyrazolone in 130 ml of methanol was added, dropwise, a solution of 1.1 ml of methylhydrazine in 20 ml of methanol and the mixture was heated at reflux for 2.5 hours.

Removal of the solvent under reduced pressure left a residual dark oil. The oil was flash chromatographed (7.5% 2-propanol in methylene chloride) to give 4,5,6,7-tetrahydro-1,7-dimethyl-1H-cyclohepta[1,2-c:3,4-c']dipyrazole as a yellow crystalline solid melting at about 94°–96° C. The chromatography also gave 4,5,6-tetrahydro-2,7-dimethyl-2H-cyclohepta[1,2-c:3,4-c')]dipyrazole melting at about 119°–121° C.

EXAMPLE 13

A solution of 0.59 ml of methylhydrazine in 20 ml of methanol was added dropwise to an ice-cold solution of 2.2 g of 4,5,6,7-tetrahydro-1,6,6-trimethyl-4-oxo-1H-indazole-5-carboxaldehyde in 80 ml of methanol. The solution was heated at reflux for 45 minutes and the solvent was removed under reduced pressure. The residue was dissolved in hot toluene and cooled to provide off-white crystals which were recrystallized from toluene to give 2,4,5,6-tetrahydro-2,4,4,6-tetramethylbenzo[1,2-c:3,4-c']dipyrazole melting at about 172°–173° C. The initial toluene mother liquor was concentrated under reduced pressure to provide tan crystals which were recrystallized from toluene to give 1,4,5,6-tetrahydro-1,4,4,6-tetramethylbenzo[1,2-c:3,4-c']dipyrazole melting at about 105°–108° C.

EXAMPLE 14

Hydrazine (0.07 ml) was added dropwise to an ice-cold solution of 0.5 g of 1-benzyl-5,6-dihydro-5-hydroxymethylene-4(1H) cyclopentapyrazolone in 25 ml of methanol. The solution was heated at reflux for 2 hours and then cooled to room temperature and stirred for 16 hours. An additional 0.07 ml of hydrazine was added and the solution was heated at reflux for 8 hours. Removal of the solvent under reduced pressure gave 1-benzyl-4,7-dihydro-1H-cyclopenta-[1,2-c:3,4-c']dipyrazole as an orange-red solid (86% yield) melting at about 61°–72° C.

EXAMPLE 15

A suspension of 6.2 g of 6-benzyl-1,4,5,6-tetrahydro-1-methylbenzo[1,2-c:3,4-c']dipyrazole in about 400 ml of liquid ammonia was prepared and sodium metal was added in small pieces until a blue or blue-green color persisted. The mixture was then stirred for 20 minutes and about 25 g of ammonium chloride was added. The ammonia was allowed to evaporate and the residue was diluted with water and extracted several times with dichloromethane. The combined dichloromethane extracts were dried over magnesium sulfate and concentrated under reduced pressure. The residue obtained was triturated in ethyl ether to give an off-white powder (78% yield) which was recrystallized from toluene to give 1,4,5,6-tetrahydro-1-methylbenzo[1,2-c:3,4-c']dipyrazole melting at about 180°–186° C.

The above reduction procedure was repeated using 5.8 g of 6-benzyl-1,4,5,6-tetrahydrobenzo[1,2-c:3,4-c']dipyrazole. The residue obtained after evaporation of the ammonia was suspended in water and the gray solid present was separated by filtration and dried (76% yield). It was then further recrystallized from water to give 1,4,5,6tetrahydrobenzo[1,2-c:3,4-c']dipyrazole as a white powder melting at about 219°–221° C.

The procedure as described in the first paragraph of this example was also used to reduce 20 g of 6-benzyl-1,4,5,6-tetrahydro-3-methylbenzo1,2-c:3,4-c']dipyrazole. The residue first obtained after evaporation of the ammonia was diluted with water and the off-white solid then present was separated by filtration (97% yield). This solid was recrystallized from aqueous ethanol to give 1,4,5,6-tetra-hydro-3-methylbenzo[1,2-c:3,4-c']dipyrazole as tan crystals melting at about 250°–252° C.

EXAMPLE 16

A solution was prepared from 5.8 g of 1-benzyl-4,7-dihydro-1H-cyclopenta[1,2-c:3,4-c']dipyrazole in 150 ml of tetrahydrofuran and 300 ml of liquid ammonia at −78° C. Sodium metal (2.8 g) was added in small pieces and the reaction was stirred at −32° C. for 1.5 hours. Ammonium chloride (10 g) was added and the ammonia was allowed to evaporate over a period of 20 minutes. The residual reaction mixture was filtered and the filter cake was washed with ethanol. The combined filtrates were then concentrated under reduced pressure and the residue was triturated with ethyl acetate to give 4,7-dihydro-1H-cyclopenta[1,2-c:3,4-c']dipyrazole as a tan granular solid (50% yield) melting at about 180° C. with decomposition

EXAMPLE 17

A solution of 14.5 g of 1,4,5,6-tetrahydro-3,6-dimethylbenzo[1,2-c:3,4-c']dipyrazole in 50 ml of dimethylformamide was added to an ice-cold stirred suspension of 2.4 g of sodium hydride in 50 ml of dimethylformamide. The reaction was stirred at 0° C. for 20 minutes and then a solution of 6.3 ml of iodomethane in 15 ml of dimethylformamide was added dropwise. The mixture was allowed to come to room temperature and stirred for 2 hours. The solvent was evaporated under reduced pressure and the residue partitioned between dichloromethane and water. The aqueous layer was extracted exhaustively with dichloromethane and the combined dichloromethane extracts were dried over magnesium sulfate and concentrated under reduced pressure. The residue was flash chromatographed (7.5% 2-propanol in dichloromethane) to give crude product. This crude mixture was dissolved in ethyl ether and acidified with ethereal hydrogen chloride. The cream color precipitate which formed was recrystallized from 2-butanol to give 1,4,5,6- tetrahydro-1,3,6-trimethylbenzo[1,2-c:3,4-c']dipyrazole monohydrochloride as light-yellow granules (20% yield) melting at about 252°–254° C.

The methylation procedure described above was repeated using 24.3 g of 1,4,5,6-tetrahydro-6-methylbenzo[1,2-c:3,4c']dipyrazole. The crude product was flash chromatographed (5% 2-propanol in dichloromethane) to give 2,4,5,6-tetra-hydro-2,6-dimethylbenzo[1,2-c:3,4-c']dipyrazole as yellow crystals (33% yield) melting at about 140°–145° C.

EXAMPLE 18

A mixture was prepared from 4 g of 1,4,5,6-tetrahydro6-methylbenzo[1,2-c:3,4-c']dipyrazole in 120 ml of decalin and 3 g of 5% palladium on charcoal was added. The mixture was heated at about 195° C. under an atmosphere of nitrogen until the dehydrogenation reaction was complete as shown by thin layer chromatography. In this case, the reaction time was 18 hours and the mixture was cooled and filtered. The filter cake was washed with hexane and then mixed with methanol. After stirring the mixture for 30 minutes, it was filtered through diatomaceous earth. The filtrate was concentrated under reduced pressure and the residue was triturated in 50:50 hexane:ethyl ether to give an off-white powder (71% yield). This was recrystallized from toluene to give 1,6-dihydro-6-methylbenzo[1,2-c:3,4-c']dipyrazole as cream-colored crystals melting at about 180°-184.5° C. This compound has the following structural formula:

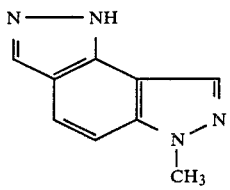

EXAMPLE 19

When the dehydrogenation procedure of Example 18 was repeated using the appropriate tetrahydrobenzodipyrazole as the starting material, the following compounds were obtained:

1,6-Dihydro-1,6 dimethylbenzo[1,2-c:3,4-c']dipyrazole as colorless needles melting at about 122.5°-124° C. The initial crude product was triturated in hexane to give a grey-white powder (82% yield) and then recrystallized from a mixture of toluene and hexane.

2,6-Dihydro-2,6-dimethylbenzo[1,2-c:3,4-c']dipyrazole as cream-colored platelets melting at about 135°-138° C. In this case, the crude product was triturated in hexane to give an off-white powder (84% yield) which was then recrystallized from a mixture of toluene and hexane.

1,6-Dihydro-3,6-dimethylbenzo[1,2-c:3,4-c']dipyrazole as a cream-colored powder melting at about 158.5°-162° C. The initial crude product was triturated in ethyl ether/hexane to give a grey solid (45% yield) which was recrystallized from toluene.

1,6-Dihydro-3,8-dimethylbenzo[1,2-c:3,4-c']dipyrazole as a light-lavender powder melting at above 290° C. The product powder (70% yield) was obtained by trituration of the crude product in hot methanol followed by cooling.

1,6-Dihydro-8-methylbenzo[1,2-c:3,4-c']dipyrazole as a white powder melting at about 249°-251° C. Recrystallization of the initial crude product from hot methanol gave the indicated product (72% yield).

1,6-Dihydrobenzo[1,2-c:3,4-c']dipyrazole as cream-colored crystals melting at greater than 290° C. with decomposition. In this case, the initial product was a grey powder (68% yield) which was recrystallized from a mixture of ethanol and water.

2,6-Dihydro-2,3,6-trimethylbenzo[1,2-c:3,4-c']dipyrazole as cream-colored crystals melting at about 128°-134° C. In this case, the initial crude product was flash chromatographed (7.5% 2-propanol in methylene chloride) to give an off-white powder (48% yield) which was recrystallized from toluene.

1,6-Dihydro-3-methylbenzo[1,2-c:3,4-c']dipyrazole melting at about 277°-279.5° C. In this case, the crude product first obtained was flash chromatographed (10% methanol in methylene chloride) to give a white powder (31% yield) which was recrystallized from a mixture of ethyl acetate and toluene.

1,6-Dihydro-1,3,6-trimethylbenzo[1,2-c:3,4-c']dipyrazole as a tan powder melting at about 93°-96° C.

1,6-Dihydro-1-methylbenzo[1,2-c:3,4-c']dipyrazole as a cream powder melting at about 252°-255° C.

What is claimed is:

1. A compound of the formula

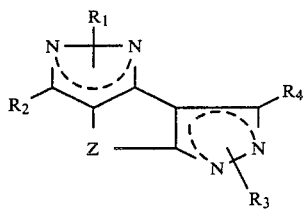

wherein $R_1$, $R_2$, $R_3$ and $R_4$ are each independently hydrogen or methyl with $R_1$ and $R_3$ being positioned on one of the nitrogens in their respective rings with the other nitrogen then being doubly bonded to the adjacent carbon; the dotted lines indicate the presence of two conjugated double bonds with the specific position of the double bonds being determined by the position of the $R_1$ or $R_3$ substituents; Z is —CH=CH— or —[$C_nH_{(2n-q)}(CH_3)_q$]— wherein n is 1, 2 or 3; q is 0, 1 or 2; and $C_nH_{(2n-q)}$ is a straight-chain alkylene.

2. A compound according to claim 1 having the formula

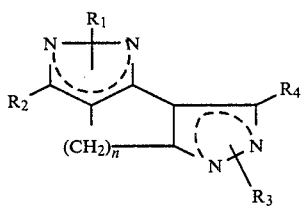

wherein $R_1$, $R_2$, $R_3$ and $R_4$ are each independently hydrogen or methyl with $R_1$ and $R_3$ being positioned on one of the nitrogens in their respective rings with the other nitrogen then being doubly bonded to the adjacent carbon; the dotted lines indicate the presence of two conjugated double bonds with the specific position of the double bonds being determined by the position of the $R_1$ or $R_3$ substituents; and n is 1, 2 or 3.

3. A compound according to claim 1 having the formula

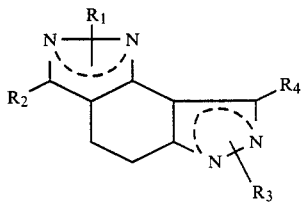

wherein $R_1$, $R_2$, $R_3$ and $R_4$ are each independently hydrogen or methyl with $R_1$ and $R_3$ being positioned on one of the nitrogens in their respective rings with the other nitrogen then being doubly bonded to the adjacent carbon; the dotted lines indicate the presence of two conjugated double bonds with the specific position of the double bonds being determined by the position of the $R_1$ or $R_3$ substituents.

4. A compound according to claim 1 having the formula

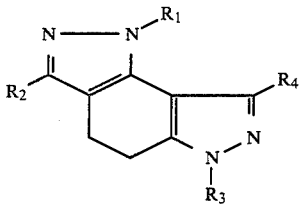

wherein $R_1$, $R_2$, $R_3$ and $R_4$ are each independently hydrogen or methyl.

5. A compound according to claim 1 which is 1,4,5,6-tetrahydro-1,6-dimethylbenzo[1,2-c:3,4-c']dipyrazole.

6. A compound according to claim 1 which is 1,4,5,6-tetrahydro-1,3,6-trimethylbenzo[1,2-c:3,4-c']dipyrazole.

7. A compound according to claim 1 which is 1,4,5,6-tetrahydro-3,6-dimethylbenzo[1,2-c:3,4-c']dipyrazole.

8. A compound according to claim 1 which is 1,4,5,6-tetrahydro-6-methylbenzo[1,2-c:3,4-c']dipyrazole.

9. A compound according to claim 1 which is 1,4,5,6-tetrahydro-3-methylbenzo1,2-c:3,4-c')dipyrazole.

10. A compound according to claim 1 which is 2,4,5,6-tetrahydro-2,3,6-trimethylbenzo[1,2-c:3,4-c']dipyrazole.

11. A compound according to claim 1 having the formula

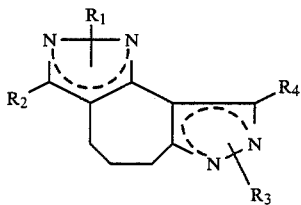

wherein $R_1$, $R_2$, $R_3$ and $R_4$ are each independently hydrogen or methyl with $R_1$ and $R_3$ being positioned on one of the nitrogens in their respective rings with the other nitrogen then being doubly bonded to the adjacent carbon; the dotted lines indicate the presence of two conjugated double bonds with the specific position of the double bonds being determined by the position of the $R_1$ or $R_3$ substituents.

12. A compound according to claim 1 which is 4,5,6,7-tetrahydro-7-methyl-1H-cyclohepta[1,2-c:3,4-c']dipyrazole.

13. A compound according to claim 1 which is 4,5,6,7-tetrahydro-2,7-dimethyl-2H-cyclohepta[1,2-c:3,4-c']-dipyrazole.

14. A compound according to claim 1 having the formula

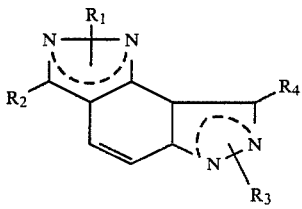

wherein $R_1$, $R_2$, $R_3$ and $R_4$ are each independently hydrogen or methyl with $R_1$ and $R_3$ being positioned on one of the nitrogen in their respective rings with the other nitrogen then being doubly bonded to the adjacent carbon; the dotted lines indicate the presence of two conjugated double bonds with the specific position of the double bonds being determined by the position of the $R_1$ or $R_3$ substituents.

15. A compound according to claim 1 which is 1,6-dihydro-3,6-dimethylbenzo[1,2-c:3,4-c']dipyrazole.

16. A compound according to claim 1 which is 2,6-dihydro-2,3,6-trimethylbenzo[1,2-c:3,4-c']dipyrazole.

17. A method for alleviating bronchial spasm in mammals which comprises administering to a mammal in need thereof a bronchodilating amount of a compound of the formula

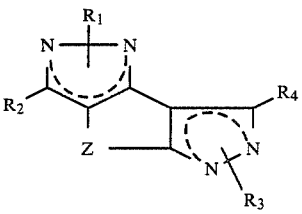

wherein $R_1$, $R_2$, $R_3$ and $R_4$ are each independently hydrogen or methyl with $R_1$ and $R_3$ being positioned on one of the nitrogens in their respective rings with the other nitrogen then being doubly bonded to the adjacent carbon; the dotted lines indicate the presence of two conjugated double bonds with the specific position of the double bonds being determined by the position of the $R_1$ or $R_3$ substituents; Z is —CH=CH— or —[$C_nH_{(2n-q)}(CH_3)_q$]— wherein n is 1, 2 or 3; q is 0, 1 or 2; and $C_nH_{(2n-q)}$ is a straight-chain alkylene.

* * * * *